US009642966B2

(12) United States Patent
Lee

(10) Patent No.: US 9,642,966 B2
(45) Date of Patent: May 9, 2017

(54) INTRAVENOUS (IV) INFUSION MONITORING METHOD AND SYSTEM

(71) Applicant: Freddie Eng Hwee Lee, Singapore (SG)

(72) Inventor: Freddie Eng Hwee Lee, Singapore (SG)

( * ) Notice: Subject to any disclaimer, the term of this patent is extended or adjusted under 35 U.S.C. 154(b) by 66 days.

(21) Appl. No.: 14/434,466

(22) PCT Filed: Oct. 30, 2013

(86) PCT No.: PCT/SG2013/000466
§ 371 (c)(1),
(2) Date: Apr. 9, 2015

(87) PCT Pub. No.: WO2014/070112
PCT Pub. Date: May 8, 2014

(65) Prior Publication Data
US 2015/0273144 A1    Oct. 1, 2015

(30) Foreign Application Priority Data
Oct. 31, 2012    (SG) .................................. 201208063

(51) Int. Cl.
*G01F 1/708*    (2006.01)
*A61M 5/168*    (2006.01)
*A61M 5/14*    (2006.01)

(52) U.S. Cl.
CPC ...... *A61M 5/16886* (2013.01); *A61M 5/1414* (2013.01); *G01F 1/7084* (2013.01);
(Continued)

(58) Field of Classification Search
CPC ............. G01F 1/7084; A61M 5/16886; A61M 5/1414; A61M 2205/18;
(Continued)

(56) References Cited

U.S. PATENT DOCUMENTS 4,384,578 A * 5/1983 Winkler ............ A61M 5/16886
    128/DIG. 13
4,532,811 A * 8/1985 Miller, Jr. ............... G01F 11/00
    73/861.95
(Continued)

FOREIGN PATENT DOCUMENTS

DE    44 04 395 A1    8/1995

OTHER PUBLICATIONS

International Search Report and Written Opinion for Application No. PCT/SG2013/000466, mailed Mar. 20, 2014.
(Continued)

*Primary Examiner* — David Bolduc
(74) *Attorney, Agent, or Firm* — Wolf, Greenfield & Sacks, P.C.

(57) ABSTRACT

In a method of determining a flow rate in an intravenous fluid delivery system according to one embodiment of the present invention, the fluid delivery channel forms a segment of the intravenous infusion system. An input thermal signal is emitted into a source location of a fluid delivery channel at an emitting instant. A first output thermal signal is received from a first sensor location of the fluid delivery channel at a first receiving instant. The first sensor location is positioned with a first interval downstream from the source location. The input thermal signal, the first output thermal signal, the emitting instant, the first receiving instant and the first interval define a first measured thermal profile. The first measured thermal profile is matched with a reference thermal profile which corresponds to a reference value, and the flow rate can be determined.

10 Claims, 12 Drawing Sheets

(52) U.S. Cl.
CPC ............ *A61M 2005/16863* (2013.01); *A61M 2205/18* (2013.01); *A61M 2205/3334* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/6072* (2013.01)

(58) Field of Classification Search
CPC ........... A61M 2205/16863; A61M 2205/3334; A61M 2205/3368; A61M 2205/3553; A61M 2205/3561; A61M 2205/3592; A61M 2205/50; A61M 2205/502; A61M 2205/52; A61M 2205/6072
See application file for complete search history.

(56) References Cited

U.S. PATENT DOCUMENTS

| | | | | |
|---|---|---|---|---|
| 4,555,940 A * | 12/1985 | Renger | ................ | G01F 1/6847 604/246 |
| 4,813,280 A * | 3/1989 | Miller, Jr. | ............. | G01F 1/7084 73/273 |
| 4,938,079 A * | 7/1990 | Goldberg | ............. | G01F 1/7084 604/65 |
| 6,089,103 A * | 7/2000 | Smith | ................... | A61B 5/028 600/486 |
| 6,169,965 B1 * | 1/2001 | Kubisiak | ............... | G01F 1/6842 374/137 |
| 6,234,016 B1 * | 5/2001 | Bonne | .................. | G01F 1/6845 73/204.26 |
| 6,380,535 B1 * | 4/2002 | Wetzel | .................. | B64D 43/02 250/227.14 |
| 7,908,931 B1 * | 3/2011 | Dam | ..................... | G01F 1/7084 73/861.05 |
| 2005/0066747 A1 * | 3/2005 | Sobek | .................. | G01F 1/7084 73/861.95 |
| 2008/0210002 A1 * | 9/2008 | Kamiunten | .......... | G01F 1/6847 73/204.23 |
| 2009/0049907 A1 * | 2/2009 | Wu | ....................... | G01F 1/6845 73/204.26 |
| 2009/0235735 A1 * | 9/2009 | Tsypko | ................. | G01F 1/6847 73/204.24 |
| 2013/0008225 A1 * | 1/2013 | Haartsen | ............... | G01F 1/7084 73/1.24 |
| 2014/0155867 A1 * | 6/2014 | Lee | ....................... | G01F 1/6847 604/533 |

OTHER PUBLICATIONS

International Preliminary Report on Patentability for Application No. PCT/SG2013/000466, mailed Jan. 20, 2015.

\* cited by examiner

| Flow Rate | T2 | | | | | | | |
|---|---|---|---|---|---|---|---|---|
| | Tp | | Amp | | Tr_80 | | Tf_80 | |
| | Mean | STD | Mean | STD | Mean | STD | Mean | STD |
| 2.0 | 22.41 | 0.96 | 3.68 | 0.12 | 16.27 | 0.31 | 34.26 | 0.68 |
| 2.1 | 22.10 | 0.93 | 3.47 | 0.13 | 16.00 | 0.31 | 33.07 | 0.64 |
| 2.2 | 21.28 | 1.19 | 3.57 | 0.13 | 15.67 | 0.46 | 31.86 | 1.33 |
| 2.3 | 20.21 | 0.61 | 3.46 | 0.07 | 14.99 | 0.24 | 30.60 | 0.62 |
| 2.4 | 19.66 | 0.36 | 3.66 | 0.06 | 14.65 | 0.16 | 29.29 | 0.37 |
| 2.5 | 19.52 | 0.76 | 3.71 | 0.17 | 14.11 | 0.25 | 28.91 | 0.83 |
| 2.6 | 17.98 | 0.67 | 3.73 | 0.74 | 13.63 | 0.52 | 26.15 | 2.28 |
| 2.7 | 17.38 | 1.23 | 3.73 | 0.56 | 13.25 | 0.92 | 25.68 | 1.91 |
| 2.8 | 16.84 | 0.47 | 3.73 | 0.23 | 12.90 | 0.18 | 25.25 | 0.85 |
| 2.9 | 16.36 | 0.38 | 3.73 | 0.21 | 12.58 | 0.32 | 24.84 | 0.70 |
| 3.0 | 15.95 | 0.27 | 3.73 | 0.10 | 12.29 | 0.18 | 24.47 | 0.50 |
| 3.1 | 15.61 | 0.24 | 3.73 | 0.08 | 12.03 | 0.12 | 24.11 | 0.45 |
| 3.2 | 15.33 | 0.38 | 3.72 | 0.31 | 11.80 | 0.27 | 23.78 | 0.81 |
| 3.3 | 15.12 | 0.17 | 3.72 | 0.11 | 11.60 | 0.07 | 23.47 | 0.31 |
| 3.4 | 15.26 | 1.67 | 3.99 | 0.92 | 11.42 | 1.04 | 22.93 | 2.94 |
| 3.5 | 15.67 | 0.28 | 3.51 | 0.06 | 11.86 | 0.22 | 22.63 | 0.49 |
| 3.6 | 15.26 | 0.69 | 3.68 | 0.15 | 11.60 | 0.39 | 22.66 | 0.66 |
| 3.7 | 15.04 | 0.45 | 3.75 | 0.18 | 11.40 | 0.37 | 21.95 | 0.40 |
| 3.8 | 14.92 | 0.38 | 3.72 | 0.16 | 11.67 | 0.21 | 21.30 | 1.02 |
| 3.9 | 15.37 | 0.85 | 3.24 | 0.21 | 11.63 | 0.46 | 22.10 | 0.86 |
| 4.0 | 15.06 | 0.32 | 3.40 | 0.08 | 11.59 | 0.19 | 21.36 | 0.69 |
| 4.1 | 14.88 | 0.70 | 3.23 | 0.15 | 11.43 | 0.31 | 21.15 | 0.86 |
| 4.2 | 14.94 | 0.24 | 3.45 | 0.06 | 11.61 | 0.22 | 20.86 | 0.58 |
| 4.3 | 15.51 | 0.55 | 3.19 | 0.11 | 11.61 | 0.14 | 22.71 | 0.52 |
| 4.4 | 15.45 | 0.45 | 3.12 | 0.04 | 11.56 | 0.16 | 22.38 | 0.55 |

FIG. 9A

INTRAVENOUS (IV) INFUSION MONITORING METHOD AND SYSTEM

RELATED CASE INFORMATION

This application is a 371 U.S. National Stage Application of International Application No. PCT/SG2013/000466, filed on Oct. 30, 2013, which claims priority to Singapore application no. 201208063-6, filed on Oct. 31, 2012, each of which is hereby incorporated by reference in its entirety.

FIELD OF INVENTION

The invention is in the field of monitoring flow rate of fluid in infusion therapy and more specifically it relates to a system means comprising of a disposable flow cell, a flow detection unit and an optional database server that allows communication of information between the patient tagged flow detection unit and a patient care provider site.

BACKGROUND OF THE INVENTION

The current invention addresses the need for a portable, disposable means of monitoring flow rate in infusion therapy especially in cases where medication administered is toxic or has a narrow therapeutic range. The measurement or monitoring of flow rate will have to be non-contact.

The measurements of heat pulse, especially via non contact means are always fraught with complexities. The impact of thermal dynamics and kinematics resulting from the interplay of thermal coefficient, thermal mass, heat loss due to emissivity and conduction of heat along the channel carrying conduit when velocity changes makes flow rate determination by measurement of flow rate by mathematical relationship derived from single or even multiple parameters limited in its applications.

The measurement of flow rate by measuring the time for heat pulse to flow between two points is known (U.S. Pat. No. 4,813,280). The flow rate is inversely proportional to the time. A flow rate range of 48 ml-144 ml/Hour (Hr) is possible by means of the flow cell construction disclosed. The fluid channel has an over sleeve which acts as barriers preventing contact between thermal probes and the fluid. Thermal probes used as heat source and sensor require very thin barriers so that the measurement accuracy is not compromised. The flow cell construction results in creating an inner diameter about 0.1 inch (2.54 mm) or a cross sectional area 4.0 mm$^2$ (smaller dimensions presumably do not allow engagement of the probes).

In U.S. Pat. No. 4,938,079, a non contact flow measurement based on the change in resonance of a microwave signal with the passage of the thermal marker is disclosed. The thermal marker could be produced by conventional heating of one with microwave radiation. The setup is complex and is intended for closed loop flow-measurement where measured output is used to adjust flow rate. The technology used renders it impractical as a mobile device.

Limitations in applications of prior art makes the creation of a device with the above mentioned requirements non existent, despite the patents were issued 20 or more years ago.

SUMMARY OF THE INVENTION

According to one embodiment of the invention, a flow cell forms a segment of the fluid channel of an IV infusion setup. The flow cell could either be an integral part of the infusion line, for example an in-line component or a separate extension that could be connected to the distal end of the infusion set up before the final connection to the patient.

The flow cell forms a fluid channel which is made from a pliable soft tube of conductive thermoplastic elastomer compressed between two rigid plates such that the cross section formed inside the tube is flat and thin, providing minimal thermal mass of the fluid passing through. The inventive is to allow a rapid thermal response so that amplitude change can be detected and that the velocity of the fluid passing through the conduit can be significantly increased to produce detectable and distinct pattern changes in the thermal profile along the length of the tube.

The rigid plates could be part of an assembly housing that gives protection to the pliable soft tube against mechanical mishandling and can be made of polycarbonate materials, polypropylene of ABS. There are windows or openings on at least one side of the housing such that the pliable soft tube is accessible. At least one opening is to allow physical contact between a soft flexible heater and the outer surface of the pliable tube. Further a plurality of opening allows the detection of infrared (IR) emission from the surface of the pliable tube.

In this invention, IR sensors are placed adjacent to the pliable tube and sense the change in the, thermal profile of the conduit when the thermal pulse passes through, there is no requirement of contact between the probe and the barrier as it is not the temperature of the fluid that is the object of measurement.

The conduit is created by compressing an extruded pliable tube of 2.0 mm or less inner diameter. The cross sectional area created is only 1.0 mm.

The smaller the cross section, the faster is the fluid velocity for a given volumetric flow in mL/Hr which permits slow flow rates to be measured. The cited patent measures flow of about 48 mL/Hr compared to the filed invention which measures flow rate as low as 1.0 mL/Hr.

In this invention, a small wearable ambulatory device (weighing about 30 grams without battery) with low power consumption and the capability to measure a wide flow rate range is desired. An accuracy level of 5-10% is acceptable in ambulatory infusion and the time to display first read should be possible within 10-15 seconds.

In a method of determining a flow rate in an intravenous fluid delivery system according to one embodiment of the present invention, the fluid delivery channel forms a segment of the intravenous infusion system. An input thermal signal is emitted into a source location of a fluid delivery channel at an emitting instant. A first output thermal signal is received from a first sensor location of the fluid delivery channel at a first receiving instant. The first sensor location is positioned with a first interval downstream from the source location. The input thermal signal, the first output thermal signal, the emitting instant, the first receiving instant and the first interval define a first measured thermal profile. The first measured thermal profile is matched with a reference thermal profile which corresponds to a reference value, and the flow rate can be determined.

During measurement, a thermal pulse is applied to the outer surface of the pliable soft tube. The IR sensors that are located in another housing, a Flow Detection Unit, are arranged lengthwise along the flow direction such that at least one IR sensor is in an upstream location relative to the heat source along the fluid channel, and one or more IR sensors are located downstream in relation to the heat source along the fluid channel. The flow cell is inserted or attached to the Flow Detection Unit when in use.

The IR sensors record temperature intensity over time at each of the specific locations along the fluid path. The program embedded in the microprocessor chip converts these inputs of time and temperature readings to specific parameters that characterize a measured thermal profile or in other words create a parametric thermal image associated to each sensor location.

The parameters used to characterize a thermal profile include the Peak Temperature Amplitude Ap, a first time period to reach the Peak Temperature Amplitude Tp, a second and third time periods to reach a predetermined portion of the Peak Temperature Amplitude at the respective rising edge TR and falling edge TF of the thermal pulse. While these 4 parameters principally describe a measured thermal profile, other parameters could also be used. For example, other types of algorithm for comparing the measured and reference profile may include weightage based parameters.

By comparing such measured thermal profiles for each of the plurality of locations along the fluid path channel with predetermined reference thermal profiles, a discreet flow rate can be ascribed to a pattern. Algorithms to establish the best matched pattern of measured thermal profiles to a discreet selection of flow rates will be employed to determine the measured flow rate.

Embodiments of the invention may further include encryption of barcodes on the Flow Cell. Information imbedded in the barcode could be used as a means for positive identification of the device used in the therapy to the patient. Other information embedded in the barcode could be the nominal or desired flow rate to which the monitored flow rate could be compared to ascertain deviations. The volume to be infused could be similarly bar coded, from which information on time to end of infusion could be obtained.

In one embodiment, the Flow Detection Unit houses a flexible heater as a source to generate a thermal pulse when the Flow Cell is inserted into its desired position. The activation of the heat pulse can be initiated by barcode encrypted onto the Flow Cell that would be read as the Flow Cell is swiped onto the slot provided in the Flow Detection Unit.

In one embodiment, the Flow Detection Unit comprises of a display e.g a graphical liquid crystal display (GLCD) with a user selectable icon driven menu containing information associated to the infusion being monitored such as flow rate, volume infused, medication dose status, time to end of infusion, etc., and other work schedule improvement means for the care giver can be displayed.

In one embodiment, the Flow Detection Unit comprises of WIFI connectivity means that allows communication of information e.g. flow rate to a remote Server. The Server houses a database that is updated with each infusion event and also a drug library, hence offering a depository of patient status and medication records for purposes of infusion management as well as tools for better real time patient care. Patient in remote home care hospices could be efficiently monitored as long as the Flow Detection Unit operates in a WIFI zone.

The inventive device maybe automatically activated when the Flow Cell is inserted or attached by a swiping action of the Flow Cell onto a slot on the Flow Detection Unit. In a hospital environment the Flow Detection Unit would automatically recognize the approved Server address and communication is established. Outside the hospital environment, the user will be prompted and guided by specific steps for the Flow Detection Unit to establish communication link with the Server via any accessible WIFI connection.

During use, the Flow Detection Unit together with the Flow Cell offers the care giver or patient a complete set of information pertaining to the infusion and is equipped with alarm features to enhance patient safety. Examples of possible adverse situations includes over/under infusion, occlusion, end of infusion and with the drug library data that is provided remotely by the Server, real-time medication dose and its level in relation to over/under dose limits.

The inventive device, in conjunction with the Server could display in one or more large screen monitors the infusion status of several patients, including alarm and alert situations. In particular, the time to end of infusion could be used by the care giver to enhance time management in caring for the patients in a planned manner. It is envisaged that the most imminent time to end can be floated up in the monitor screen in a nursing station, in a similar fashion to an airplane flight departure screen found in airport terminals.

BRIEF DESCRIPTION OF DRAWINGS

FIGS. 9A, 9B and 9C are Matrixes for associating reference thermal profiles to discreet flow rates.

DETAILED DESCRIPTION OF THE INVENTION

Figure 1:
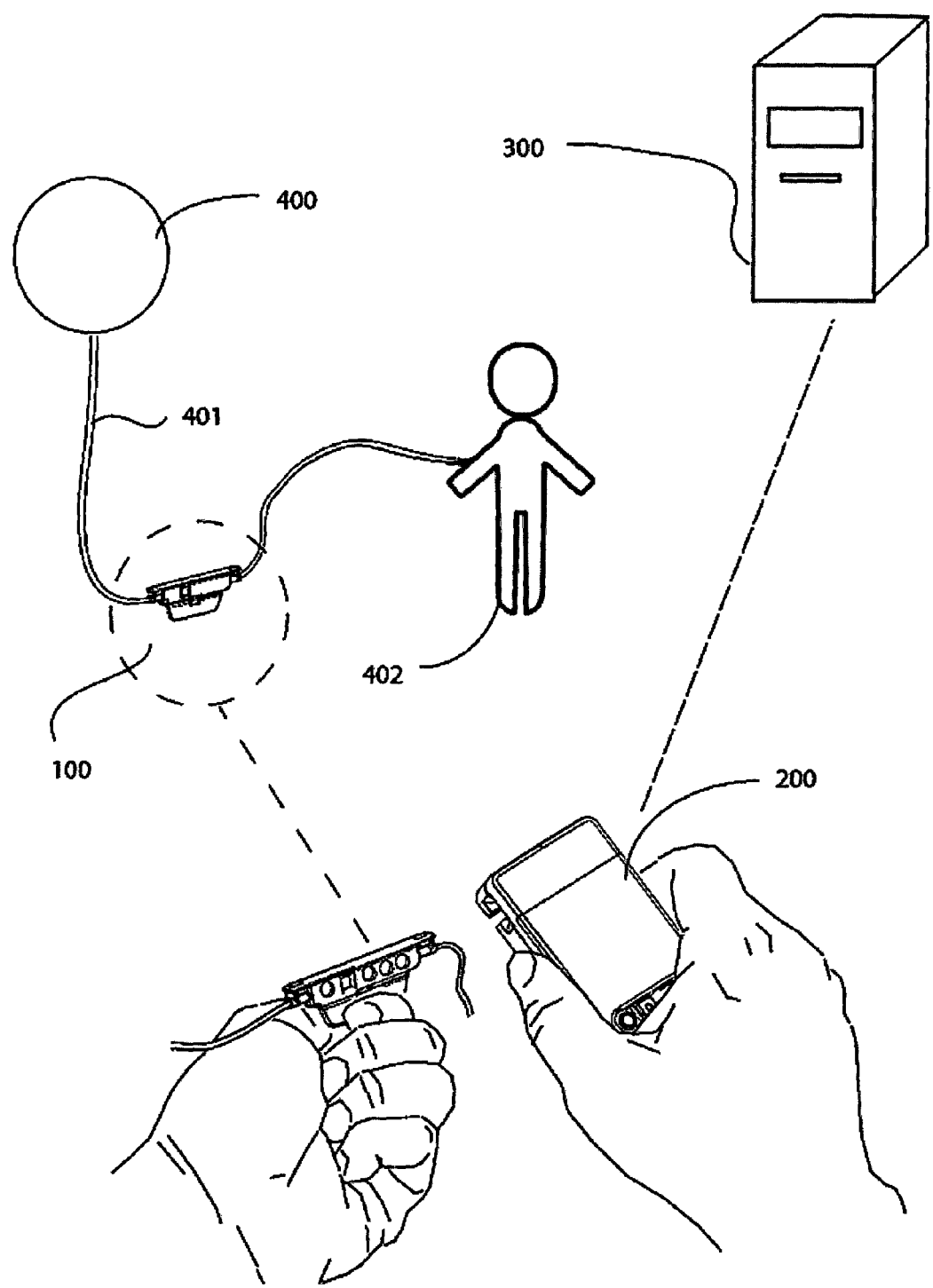
FIG. 1 is a schematic illustrating an IV monitoring system according to one embodiment of the present invention.

Referring to FIG. 1, a preferred embodiment of the apparatus of the invention has a Flow Cell 100 as an in line segment of an IV infusion elastomeric pump or any infusion line, a Flow Detection Unit 200 to which the Flow Cell 100 will be attached and an optional remote Server 300 which is in wireless communication with the Flow Detection Unit 200.

Further referring to FIG. 1, in another embodiment, the Flow Cell 100 could be a segment of a separate extension tube that could be attached to one section of an IV infusion line 401 between a pump source 400 and a patient 402. The infusion line referred to is the conduit through which medication is administered to the patient.

Figure 2:
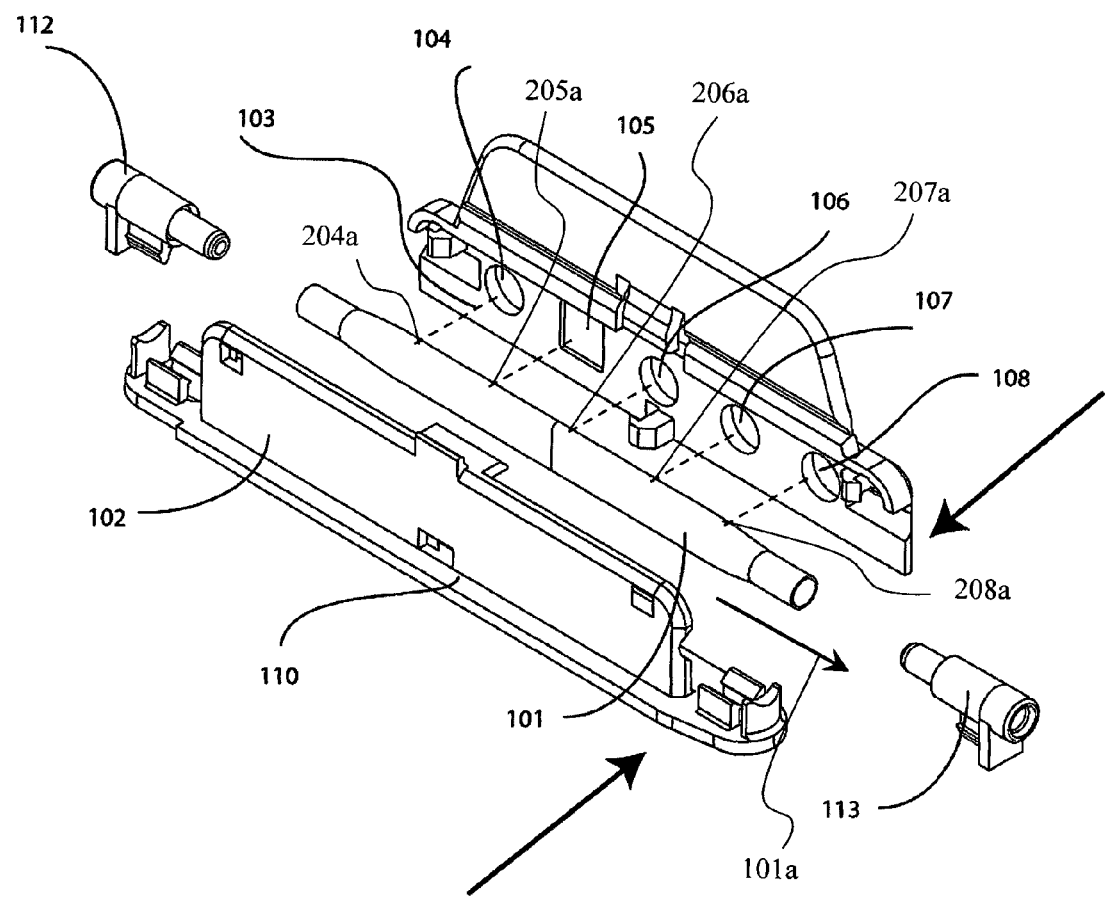
FIG. 2 is an exploded perspective view of the Flow Cell showing how the pliable soft tube is compressed between two rigid walls.

Referring to FIG. 2, according to a preferred embodiment, Flow Cell 100 includes a pliable soft tube 101 compressed between two rigid walls 102 and 103, and connected to an infusion line by fittings 112, 113. The distance between the rigid walls 102, 103 is less than the outer diameter of the tube 101, such that the cross section of the pliable tube 101 perpendicular to the direction of fluid flow created from this configuration is approximately 0.5 mm depth. For any given depth dimension, there will be ideal limits for the width of the tube as larger width may encourage the formation of air bubbles that could distort the thermal profiles formed along the length of the tube.

Further referring to FIG. 2, in one embodiment, rigid wall 103 of Flow Cell 100 has a plurality of openings 104, 105, 106, 107 and 108 through which the pliable compressed tube is accessible. When pliable tube 101 is clamped between rigid walls 102 and 103, opening 105 becomes in alignment with a source location 205a of pliable tube 101. Opening 105 allows an input thermal signal to be emitted at source location 205a from a flexible heater 205 (FIG. 3B) into the compressed pliable tube 101 at an emitting instant. The flexible heater 205 is mounted on a movable actuator 215 (FIG. 3B) that limits the forward and backward movement of the flexible heater such that the surface contact achieved is consistent. The openings 104, 106, 107 and 108 allows a more or less unobstructed detection of infra red waves on the adjacent sections of the pliable soft tube 101 when the Flow Cell 100 is at the desired position within the Flow Detection Unit 200.

Further referring to FIG. 2, in one embodiment, rigid wall 102 of Flow Cell 100 has a flange 110 set longitudinally along its edge such that a barcode 211 (FIG. 3B) can be encrypted on its surface. The information in the barcode allows flow rate references, infusion volume information or other device unique identification to be transmitted to a dedicated Server by wireless communication means.

Figure 3A:
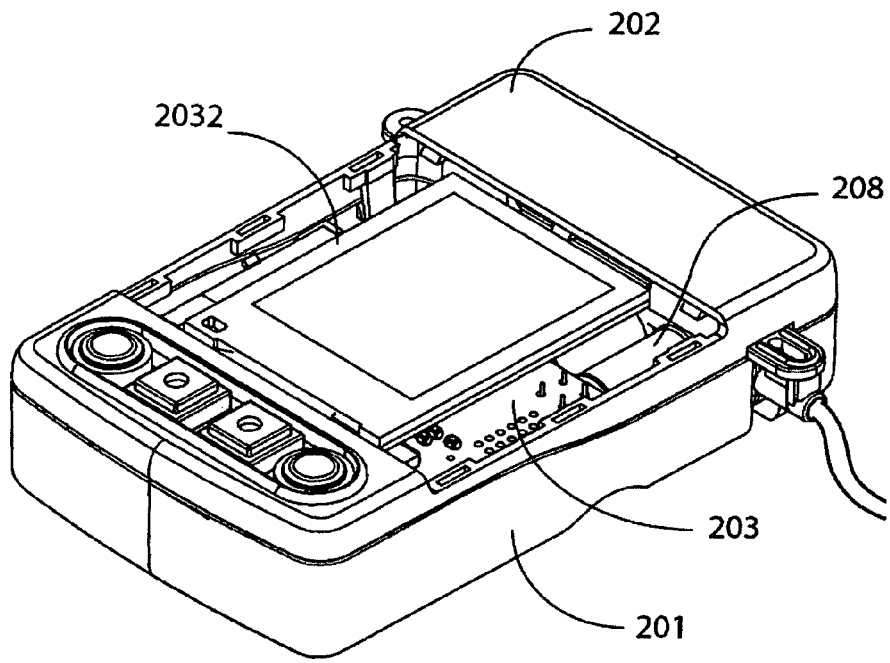
FIG. 3A is a perspective view of the Flow Detection Unit with Flow Cell in its intended position during Flow Rate monitoring.
Figure 3B:
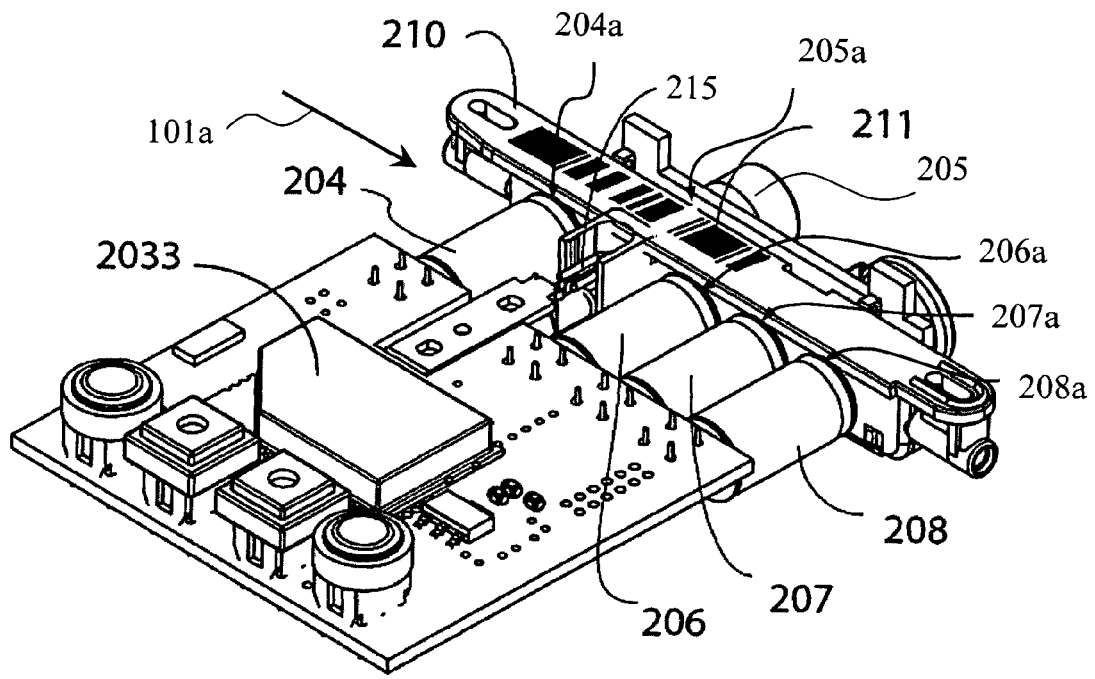
FIG. 3B is a perspective view of the infra red sensors and heater assembly in relation to the Flow Cell.
Figure 3C:
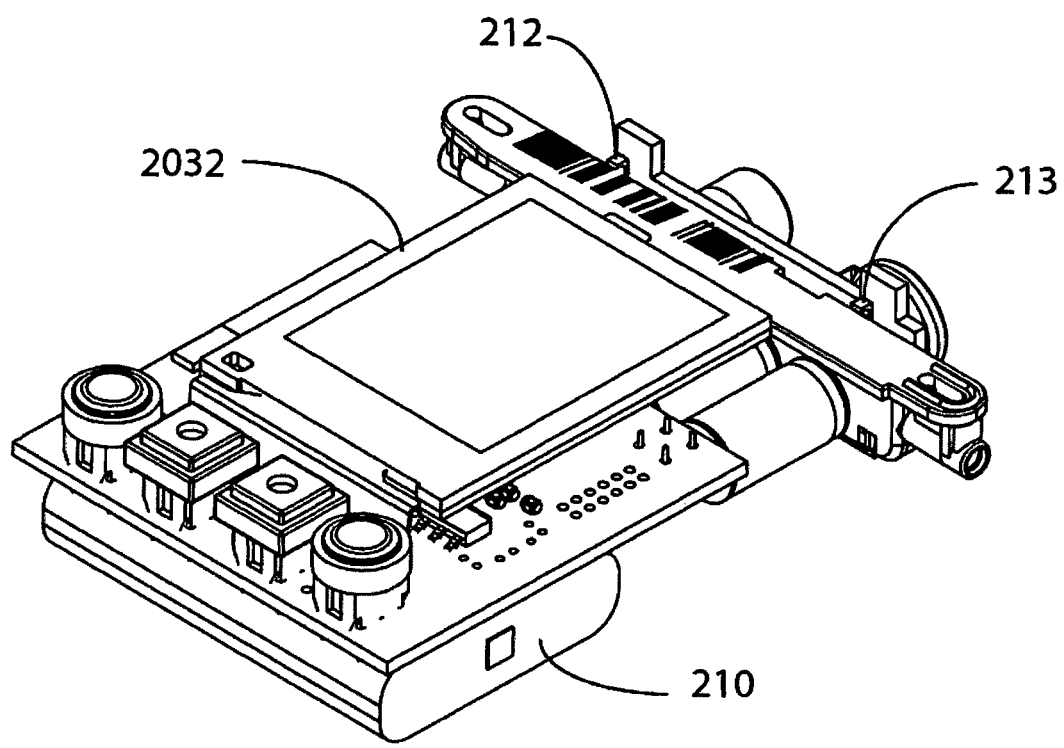
FIG. 3C is another perspective view of the Flow Detection Unit of FIG. 3A.

Referring to FIG. 3A, FIG. 3B and FIG. 3C, the housing of the Flow Detection Unit 200 has 2 halves, i.e. a lower case 201 and an upper case 202, both made from injection molded rigid plastics. The lower case 201 has a rectangular container like configuration that houses a printed circuit board 203, a battery 210, optical readers 212 and 213, infra red sensors 204, 206, 207 and 208, flexible heater and actuator 215. The infra red sensors are rigidly installed in cradle like cavities formed within the lower case 201, the flexible heater 205 mounted onto the actuator 215 is similar rigidly secured onto the inner surface of the lower case 201. Such installation ensures mechanical robustness and reduces risk of movement or misalignment of these components with the Flow Cell 100 during use.

Further referring to FIG. 3B, at least one infra red sensor, in this instance infra red checking sensor 204, is located at a checking sensor location 204a upstream along the direction 101a of the fluid flow with respect to the position of the flexible heater 205. The other one or more infra red sensors, the exact number being dependent on the range of flow rate that is intended to be determined and also design specification with respect to the physical size of the device, is/are located downstream along the direction 101a of the fluid flow with respect to the position of the flexible heater 205. In the present embodiment, a first sensor 206 is positioned at a first sensor location 206a of pliable tube 101 downstream of the source location 205a for receiving a first output thermal signal at the first sensor location 206a at a first receiving instant. In other embodiments where more sensors are used, a second sensor 207 is positioned at a second sensor location 207a of pliable tube 101 downstream of the source location 205a for receiving a second output thermal signal at the second sensor location 207a at a second receiving instant. Likewise, a third sensor 208 may be positioned at a third sensor location 208a of pliable tube 101 downstream of the source location 205a for receiving a third output signal at the third sensor location 208a at a third receiving instant. The downstream one or more sensors allow a pattern of thermal profiles to be established for each discreet velocity of fluid flow through the compressed pliable soft tube 101. The thermal profile associated to the tube surface adjacent to the upstream infra red checking sensor 204 will be distinctly different from all thermal profiles associated to downstream sensors, when there is fluid flowing. In the event of no flow or occlusion, the thermal profile associated to checking sensor 204 will resemble the thermal image at sensor 206 since sensors 204 and 206 are located equal distance apart from the flexible heater 205. Alternatively, a temperature difference between the sensors 204 and 206 may be compared with a trigger level to determine an occlusion situation.

Figure 4:
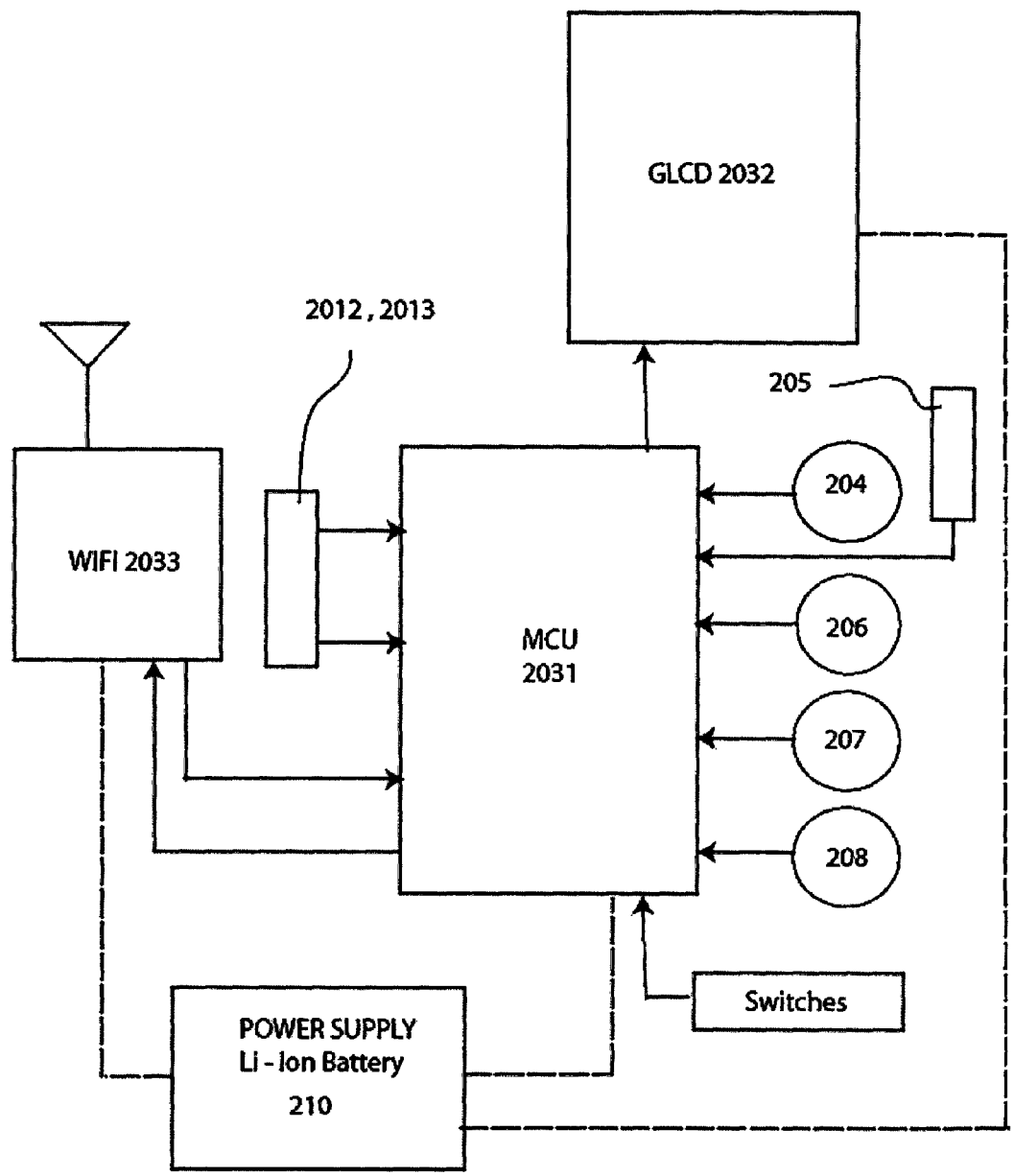
FIG. 4 is a schematic diagram of the Flow Detection Unit of FIG. 3A.

Referring to FIG. 4, the functional block diagram of the components used on printed circuit board is shown. The infra red sensors detect temperature as a function of time for each of the location of the Flow Cell that is and serves as input to the microprocessor (MCU) 2031. The programmed MCU 2031 will create measured thermal profiles for each of the sensor locations by characterizing these thermal profiles in parameters. Using a matrix that is pre-populated with reference values, e.g. discreet flow rates and its associated reference thermal profiles for each sensor locations, an unknown flow rate with its associated pattern of measured thermal profiles can be matched with a reference thermal profile which corresponds to a known discreet flow rates by means of an algorithm that selects a closest resemblance of the patterns between the measured thermal profile and the reference thermal profile. The algorithm includes identification of a match between each of the measured parameters to the reference values specific for the sensor location, such that the similarity between the measured value and reference value is quantifiable. Further, the algorithm allows the parameters to adaptively contribute to the determination of flow rate such that one of the parameters applied to a corresponding determination changes with each successive step of receiving a first output thermal signal during the flow rate determining process.

Further referring to FIG. 4, the output from MCU 2031 will be displayed by means of a GLCD 2032. In addition, these outputs will be processed for wireless transmission by a WIFI chip 2033 to the Server 300. Other data transmitted via the WIFI chip 2033 includes alarms and alerts to signal adverse infusion status. It also provides the pathway between MCU 2031 and the Server 300 to receive preset codes and information from the Server as part of device recognition protocol and also drug library information for determination of overdose situations.

Further referring to FIG. 4, a rechargeable Li-ion battery 210 allows the Flow Detection Unit to be used as a mobile ambulatory device. The optical sensors 212 and 213 (FIGS. 3B, 3C) function as barcode readers and also confirmation of the correct position of the Flow Cell 100.

Figure 5:
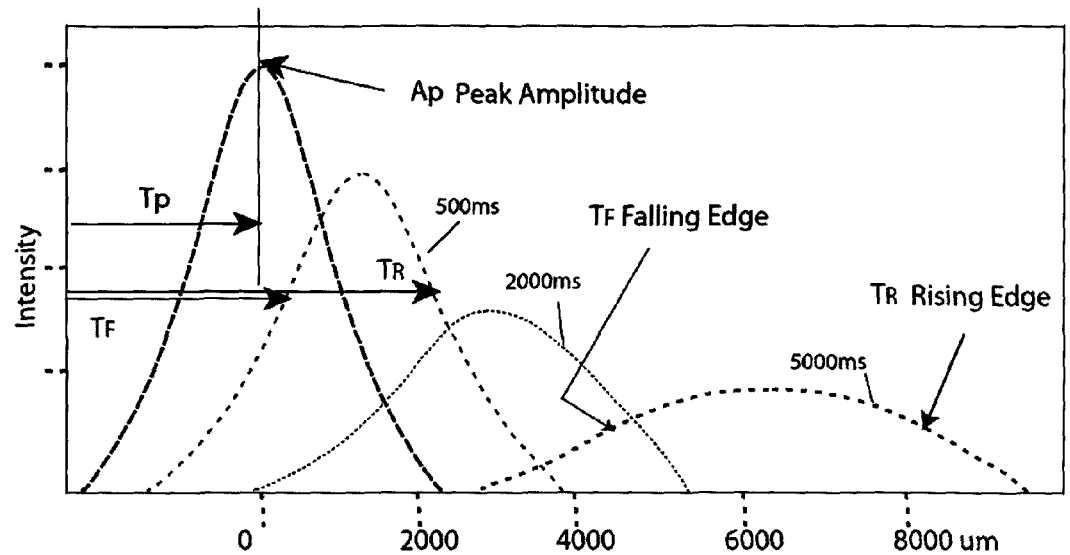
FIG. 5 is a curve showing a profile of a thermal pulse of a fluid flowing through a channel at a rate of 0.5 mL/Hr.

Referring to FIG. 5, in one embodiment of the invention, a thermal profile of a pulse is formed by defining it with its Peak Amplitude Ap, a first Time period Tp to reach Peak Amplitude, a second Time period Tr for the Leading or Rising Edge of the profile to reach a predetermined level, for instance 80% of Peak Amplitude, and a third Time period Tf for the Trailing or Falling Edge to reach the predetermined level, for instance 80% of Peak Amplitude. It is noted that the 80% level is an arbitrary level that could vary depending on factors that influence the thermal characteristics of the measurement. Generally, the thermal profile of a pulse moving at a specific velocity exhibits changes in its Peak Amplitude Ap or synonymously the area of maximum intense radiation. There is also a displacement of this Peak Amplitude Ap in relation to time, which in this embodiment is expressed as Time to reach Peak Amplitude, i.e. first time period Tp. There is also a displacement of both the Leading/Rising edge and Trailing/Falling edge away from its original position in relation to the Peak Amplitude Ap as the pulse travels away from its original position. Instead of images generated by black body cameras, these thermal profiles could be inventively represented by the chosen set of parameters.

Figure 6:
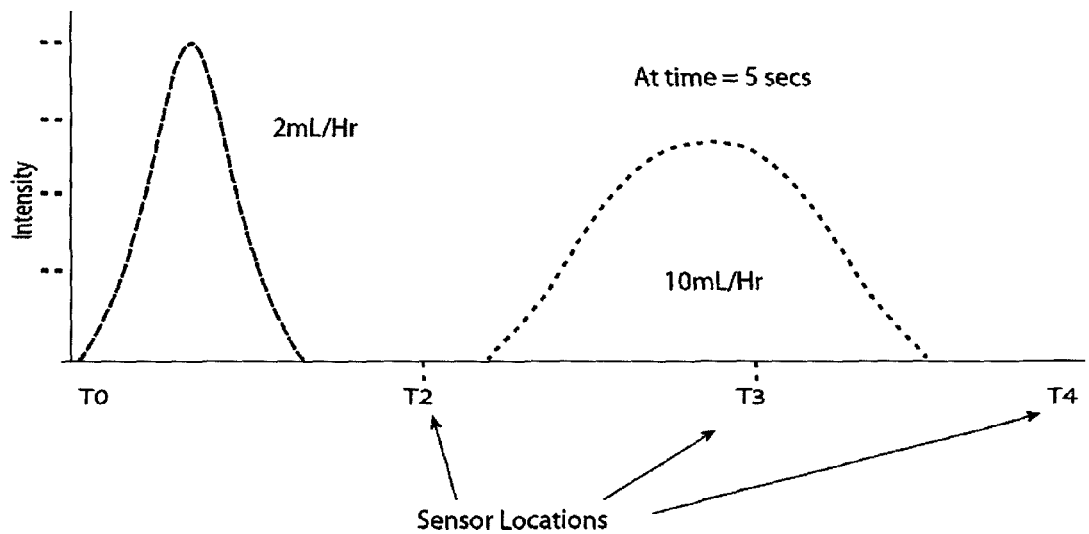
FIG. 6 is a curve showing a profile of two thermal pulses flowing at 2 different rates through a fluid channel at time=5 second after a heat pulse is applied.

Referring to FIG. 6, thermal profiles of a pulse flowing at 2 mL/Hr and 10 mL/Hr is shown at an instance 5 seconds after the thermal pulse is activated at location T0. The 2 mL/hr pulse is generally narrow and has a higher Peak Amplitude Ap as the heat applied has more time to produce a rise in temperature compared to a situation where the flow rate is faster. The 10 mL/hr pulse is generally wider and has a lower Peak Amplitude Ap for similar reasons.

Figure 7:
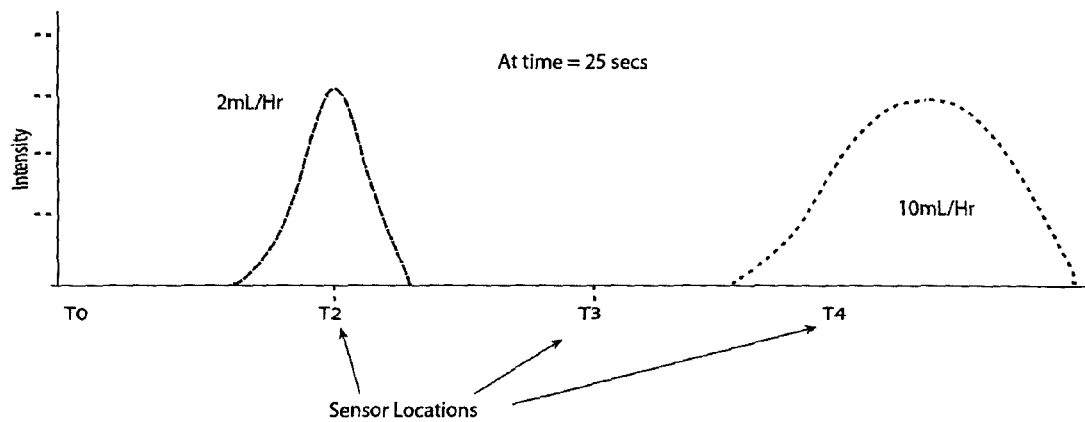
FIG. 7 is a curve showing a profile of two thermal pulses flowing at two different rates through a fluid channel at time=25 second after a heat pulse is applied.

Referring to FIG. 7, the thermal profiles described in FIG. 5 is shown at an instance 25 seconds after the thermal pulse is activated. The 2 mL/hr pulse has attenuated significantly even though it has not moved much away from its earlier position. The shape of the pulse has also changed significantly as manifested in both the Leading/Rising edge and Trailing/Falling edge of the pulse. The 10 mL/hr pulse has a much less attenuation and more subdued change in its shape, but its position when measured by the Time to reach Peak Amplitude Tp would have shown a marked displacement from compared to the 2 mL/Hr pulse due to its faster velocity.

Figure 8:
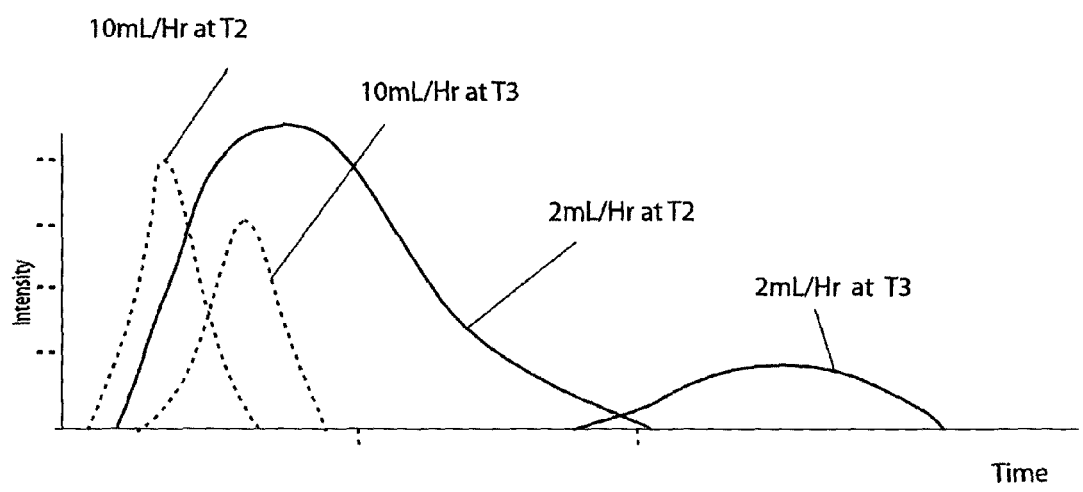
FIG. 8 is a curve showing a Time Series of thermal profiles of two pulses flowing at different rates through a fluid channel at two sensor locations.

Referring to FIG. 8, a time series of thermal profiles of 2 pulses recorded at 2 downstream sensor locations T2 and T3 is shown. In one embodiment of this invention, T2 and T3 are sensor locations 10 mm apart. The thermal profiles for the 2 mL/Hr pulse exhibit a significant change in its Peak Amplitude Ap. The change in Time to reach the Peak Amplitude Tp for the 2 sensor locations, as well as changes in the Leading and Trailing edge of the pulse are also markedly significant. As a contrast all the changes in the parameters for the 10 mL/Hr pulse is more subdued.

Figure 9B:
Figure 9C:
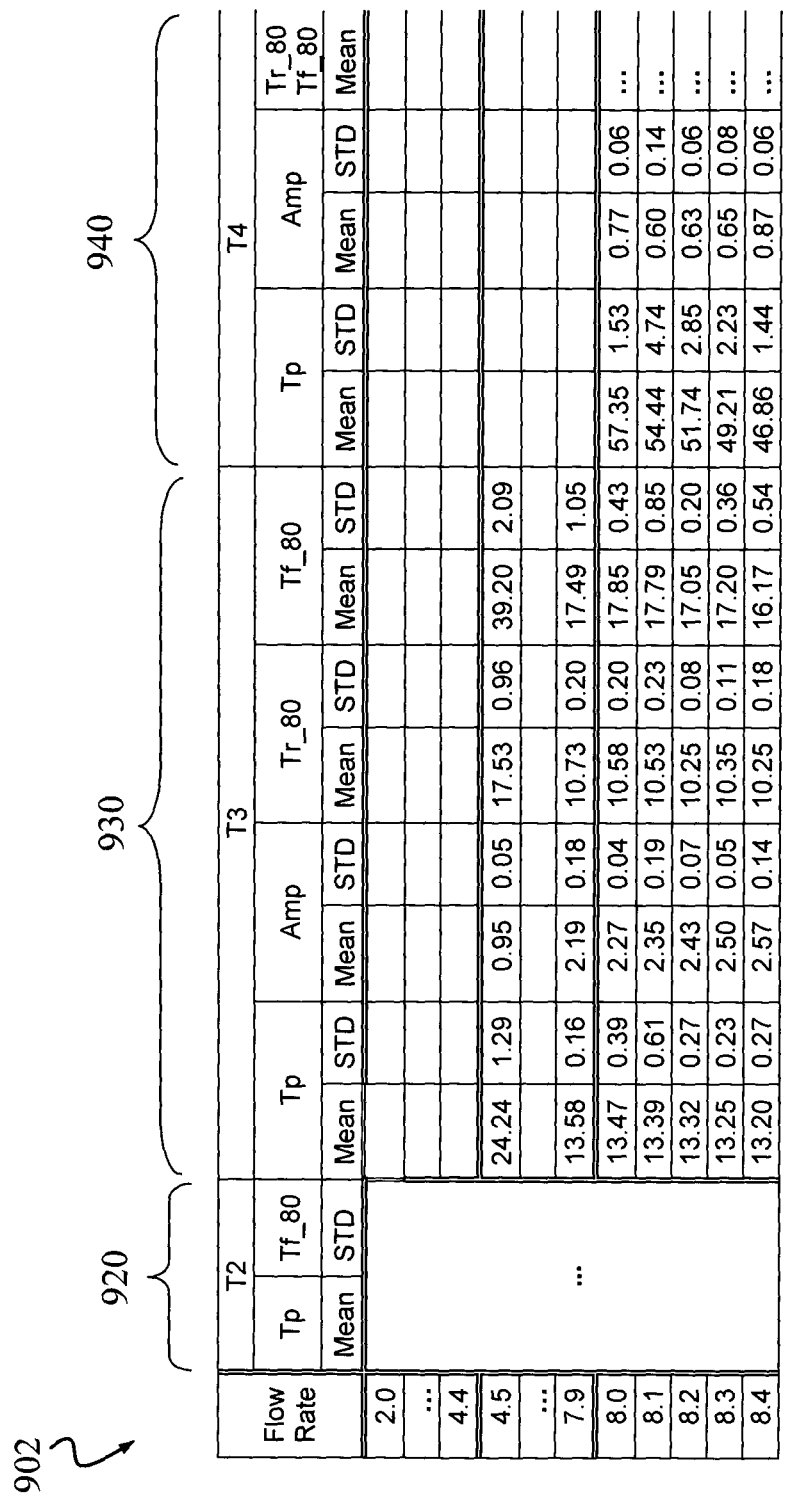

FIGS. 9A, 9B and 9C show sections of one possible Matrix 902 used to establish an association between patterns of reference thermal profiles across the sensor location and predetermined discreet flow rates. The columns represent the parameters chosen to characterize the thermal profiles recorded at each of the sensor locations. Column 910 includes reference values, i.e. known discreet flow rates. Columns 920 represents parameters associated with thermal sensor readings at first sensor location 206a. Under columns 920, columns 922 show the mean value (Mean) and standard deviation (STD) of the first time period Tp to reach the Peak Temperature Amplitude Ap. Columns 924 show the mean value and standard deviation of the Peak Temperature Amplitude Ap. Columns 926 show the mean value and standard deviation of the second time period $Tr_{-80\ for\ the\ leading\ edge\ to\ fall\ to}$ 80% of the Peak Temperature Amplitude. Columns 928 show the mean value and standard deviation of the third time period $Tf_{-80\ for\ the\ trailing\ edge\ to\ fall\ to}$ 80% of the Peak Temperature Amplitude. In one embodiment of this invention, there is one sensor located upstream with respect to the heat source located at T0, and one sensor located downstream of the heat source at T2. In other embodiments, two or more sensors are located downstream of the heat source at, e.g. T3, T4, etc. The parameters chosen are Peak Amplitude Ap, first Time period to reach Peak Amplitude Tp, second Time period Tr for Leading (Rising) Edge to reach 80% of Peak Amplitude and third Time period Tf for Trailing (Falling) edge to reach 80% of Peak Amplitude. All the parameters taken together describe the shape of the thermal profile for each sensor location. The Matrix is stored in the MCU memory and the values of the cells in the matrix are compared with measured thermal profiles quantities. When a measured thermal profile matches a reference thermal profile, the discreet flow rate corresponding to the matched reference thermal profile is selected as the actual flow rate under measurement.

The rows in the Matrix represent predetermined flow rates, consistent with the range of fluid flow rates used typically in infusion therapy. In this embodiment, the flow rates range from 2 mL/Hr to 100 mL/Hr. The incremental steps are 0.1 mL/Hr for low flow rates (below 10 mL/Hr) and for higher flow rates it increases to 1 mL/Hr (from 10 mL/Hr to 50 mL/Hr) to 5 mL/Hr (from 50 mL/Hr to 100 mL/Hr).

Figure 10:
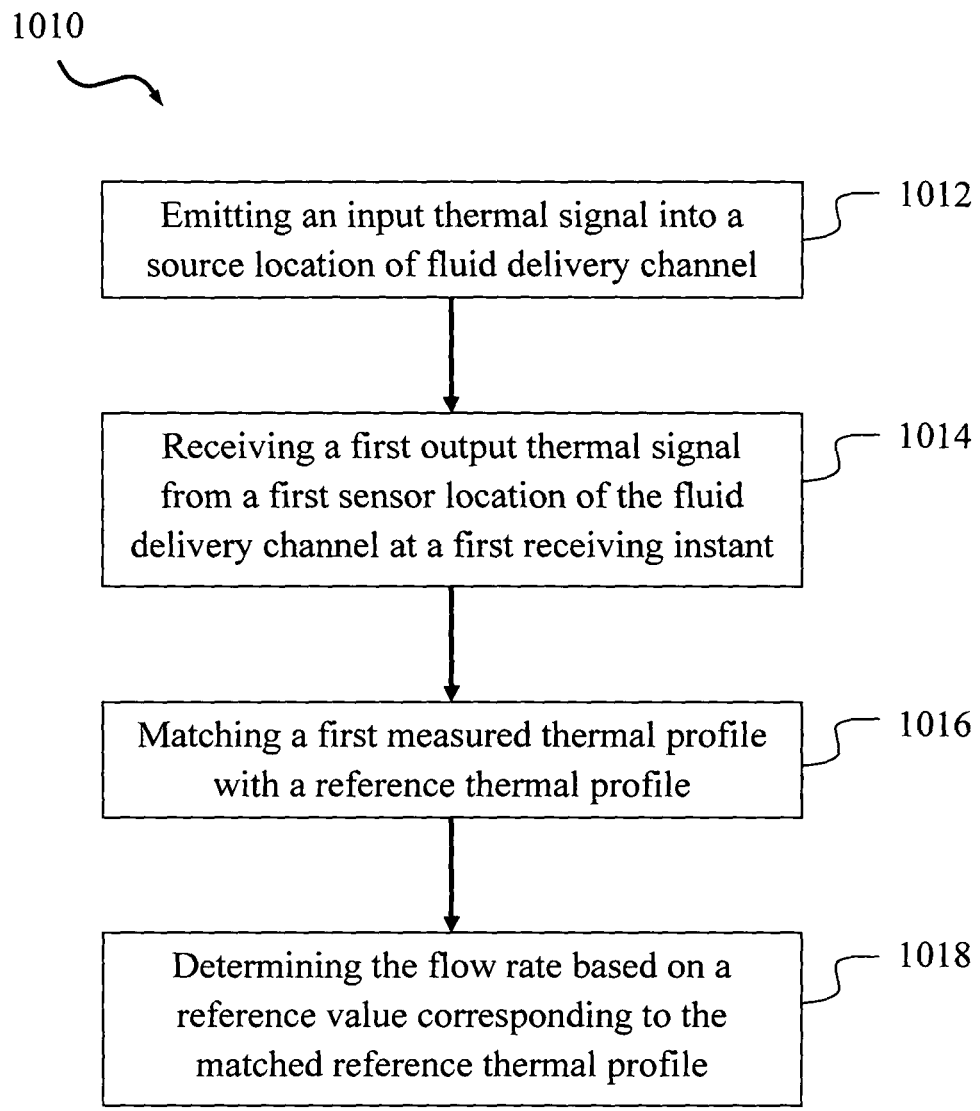
FIG. 10 is a block diagram showing a method for flow rate determination according to one embodiment of the present invention.

In the process 1010 of flow rate determination, as shown in FIG. 10, at block 1012, an input thermal signal is emitted into a source location of a fluid delivery channel at an emitting instant. At block 1014, a first output thermal signal is received from a first sensor location of the fluid delivery channel at a first receiving instant. The input thermal signal, the first output thermal signal, the emitting instant, the first receiving instant and the first interval define a first measured thermal profile. At block 1016, the first measured thermal profile is matched with a reference thermal profile which corresponds to a reference value, and the flow rate can be determined at block 1018. When matching the first measured thermal profile with the reference thermal profile, the relevant cells in matrix 902 (FIGS. 9A, 9B and 9C) for each parameter associated with the specific sensor locations will be compared to determine the best resemblance between a measured thermal profile and a reference thermal profile recorded with the relevant possibilities represented in the Matrix. In one embodiment, the algorithm specifies that each deviation between measured parameter value and the reference value is expressed in units or fraction of standard deviation for the cell concerned. The smallest deviation obtained by summing the normalized deviations will be selected to represent the best resemblance.

As an example for illustration, as shown in FIG. 9A, an unknown flow rate with readings of Tp=17.7, Ap=3.73 Tr=13.5 and Tf=26.0 will be fitted into Matrix 902 between a first minimum upper time limit 922a (mean value 17.98), and a first maximum lower time limit 922b (mean value 17.38), under column 922, mean value. Accordingly, a first reference thermal profile 920a containing first minimum upper time limit 922a is selected and the corresponding flow rate 2.6 mL/Hr in cell 912a becomes one candidate of the actual flow rate under measurement. Similarly, a second reference thermal profile 920b containing first maximum lower time limit 922b is selected and the corresponding flow rate 2.7 mL/Hr in cell 912b becomes another candidate of the actual flow rate under measurement. The algorithm selects 2.7 mL/Hr as the actual flow rate by further calculation based on the total deviations, as illustrated below:
For 2.6 mL/Hr flow rate, a total deviation of 0.7337 is derived by a sum of the following deviation calculations:

Tp std=|17.7-17.98|/0.67=0.4179

Apstd=|3.73-3.73|/0.74=0

Trstd=|13.5-13.63|/0.52=0.2500

Tfstd=|26.0-26.15|/2.28=0.0658

For 2.7 mL/Hr flow rate, a total deviation of 0.6994 is derived by a sum of the following deviation calculations:

Tp std =|17.7-17.38|/1.23=0.2602

Apstd=|3.73-3.73|/0.56=0

Trstd=|13.5-13.25|/0.92=0.2717

Tfstd=|26.0-25.68|1.91=0.1675

As the total deviation of the latter, 0.6994, is less than that in the former, 0.7337, the predetermined discreet flow rate corresponding to the reference thermal profile having the lesser deviation, i.e. 2.7 mL/Hr in this example, is determined as the actual flow rate under measurement.

In situations where the actual flow rate under measurement is expected to be in a greater range, e.g. one which is greater than 4.5 mL/Hr, a second reference thermal profile corresponding to a subsequent sensor location 207a, is provided in Matrix 902 under columns 930, as shown in FIG. 9B. The second reference thermal profile may be used in combination with the first reference thermal profile for being matched by a measured thermal profile to determine an actual flow rate in this range, with a relatively higher accuracy.

Likewise, when a much greater flow rate is to be determined, e.g. one greater than 8 mL/Hr, a further reference thermal profile corresponding to a further sensor location 208a, is provided in Matrix 902 under columns 940, as shown in FIG. 9C (sample cell data under columns 920 are omitted). The further reference thermal profile may be used in combination with the first and second reference thermal profiles for being matched by a measured thermal profile to determine an actual flow rate in this range, with a relatively higher accuracy.

The inventive idea in this method of determining flow rate acknowledges the fact that for the purpose of monitoring infusion the flow rate sensitivity required to alert adverse situations can be specified, hence obviating the need to employ methods to determine flow rates within a continuous spectrum. All prior art did not exploit this opportunity.

Figure 11:
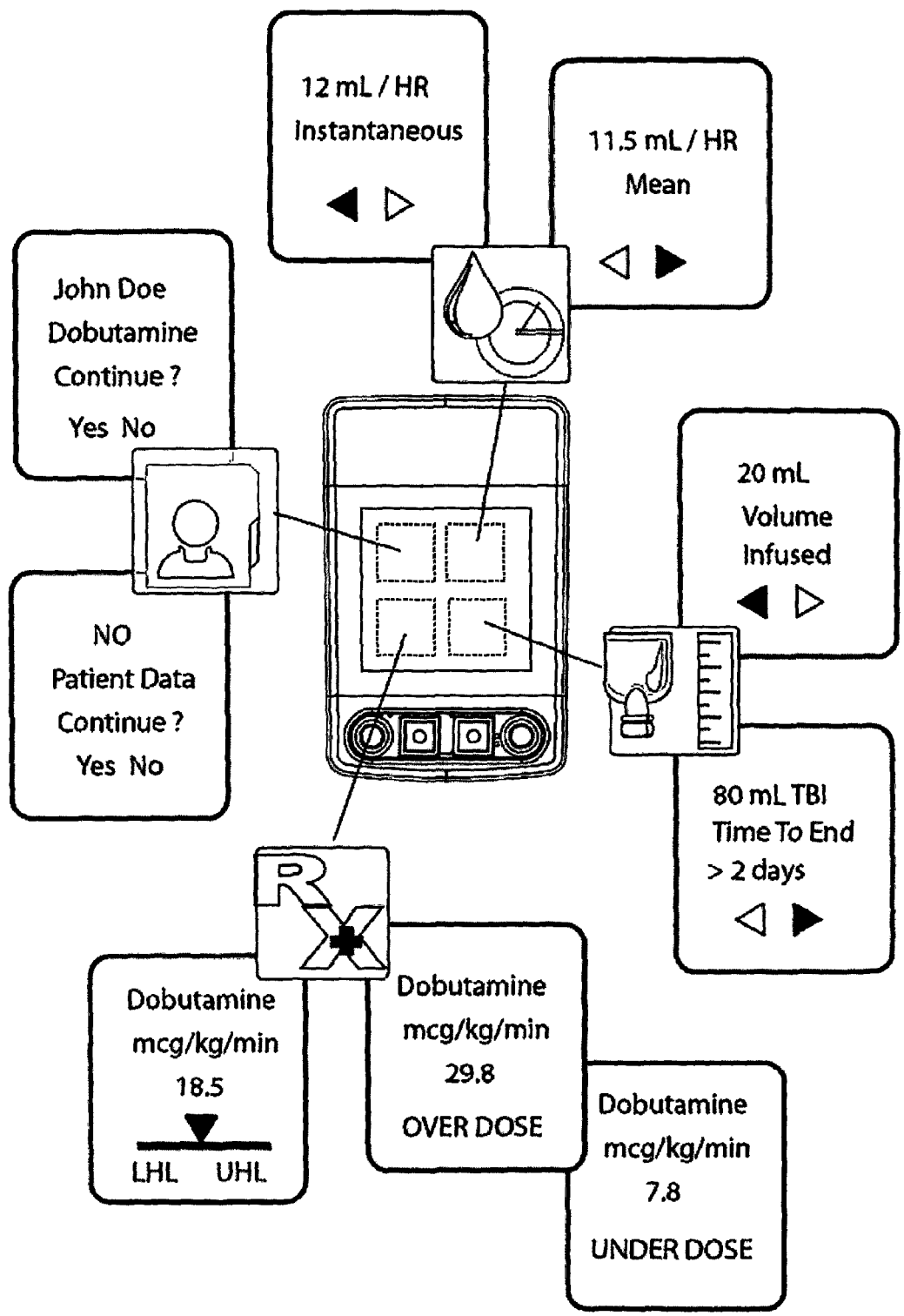
FIG. 11 is a schematic diagram showing an Example of a data screen of the Flow Detection Unit of FIG. 3A related to IV Infusion Status.

Referring to FIG. 11, in one embodiment the graphic user interface offers a selection of 4 icons with its corresponding data and information folders. The navigation through the menu is provided by push buttons, this could be replaced by touch screen features instead.

The invention claimed is:

1. A method of determining a flow rate in an intravenous fluid delivery system, the method comprising: emitting an input thermal signal into a source location of a fluid delivery channel at an emitting instant, wherein the fluid delivery channel forms a segment of the intravenous infusion system; receiving a first output thermal signal from a first sensor location of the fluid delivery channel at a first receiving instant, the first sensor location being positioned with a first interval downstream from the source location, wherein the input thermal signal, the first output thermal signal, the emitting instant, the first receiving instant and the first interval define a first measured thermal profile, and matching the first measured thermal profile with a reference thermal profile provided in a matrix, wherein the flow rate is determined based on an algorithm that selects a closest resemblance between the first measured thermal profile and the reference thermal profile;

wherein the first measured thermal profile includes at least one of a peak temperature amplitude, a first time period to reach the peak temperature amplitude, a second time period for a leading edge to reach a predetermined level of the peak temperature amplitude, and a third time period for a trailing edge to reach the predetermined level of the peak temperature amplitude;

wherein matching the first measured thermal profile with a reference thermal profile comprising: locating in the matrix a first minimum upper time limit and a first maximum lower time limit within which the first time period fits; locating in the matrix an upper temperature value corresponding to the first minimum upper time limit and a lower temperature value corresponding to the first maximum lower time limit; locating in the matrix a second upper time limit corresponding to the first minimum upper time limit and a second lower time limit corresponding to the first maximum lower time limit; locating in the matrix a third upper time limit corresponding to the first minimum upper time limit and a third lower time limit corresponding to the first maximum lower time limit; deriving an upper total deviation based on a sum of a first upper time deviation, an upper temperature deviation, a second upper time deviation and a third upper time deviation, deriving a lower total deviation based on a sum of a first, lower time deviation, a lower temperature deviation, a second lower time deviation and a third lower time deviation, wherein the reference thermal profile is one corresponding to the lesser of the upper total deviation and the lower total deviation.

2. The method of claim 1, wherein the first upper time deviation is calculated from the first minimum upper time limit and the first time period, the upper temperature deviation is calculated from the upper temperature value and the peak temperature amplitude; the second upper time deviation is calculated from the second upper time limit and the second time period; the third upper time deviation is calculated from the third upper time limit and the third time period, the first lower time deviation is calculated from the first maximum lower time limit and the first time period, the lower temperature deviation is calculated from the lower temperature value and the peak temperature amplitude; the second lower time deviation is calculated from the second lower time limit and the second time period; the third lower time deviation is calculated from the third lower time limit and the third time period.

3. The method of claim 1, further comprising receiving a second output thermal signal from a second sensor location of the fluid delivery channel at a second receiving instant, the second sensor location being positioned with a second interval downstream from the first sensor location, wherein the second output signal, the second receiving instant and the second interval define a second measured thermal profile, and matching the first and second measured thermal profiles with the reference thermal profile.

4. The method of claim 3, further comprising receiving a third output thermal signal from a third sensor location of the fluid delivery channel at a third receiving instant, the third sensor location being positioned with a third interval downstream from the second sensor location, wherein the measured thermal profile being further defined by the third output thermal signal, the third receiving instant and the third interval, and matching the first, the second and the third measured thermal profiles with the reference thermal profile.

5. The method of claim 1, further comprising receiving a checking output thermal signal from a checking sensor location of the fluid delivery channel, the checking sensor location being positioned upstream from the source location, and comparing a temperature difference between the first output thermal signal and the checking output thermal signal with a trigger level to determine an occlusion situation.

6. The method of claim 1, further comprising receiving a checking output thermal signal from a checking sensor location of the fluid delivery channel, the checking sensor location being positioned upstream from the source location, and comparing a checking thermal profile established at the checking sensor location with the first measured thermal profile to determine an occlusion situation.

7. The method of claim 1, wherein the matrix includes a plurality of reference values within a first range, each reference value corresponds to a reference thermal profile established at the first sensor location.

8. The method of claim 7, wherein the matrix includes a plurality of reference values within a second range, each reference value corresponds to a reference thermal profile established at the first and the second sensor location.

9. The method of claim 1, wherein the algorithm includes identification of a match between at least the first measured thermal profile to the reference thermal profile specific for the first sensor location, such that a comparison between the first measured thermal profile and reference thermal profile is quantifiable.

10. The method of claim 1, wherein the first measured thermal profile is defined by parameters including the input thermal signal, the first output thermal signal, the emitting instant, the first receiving instant and the first interval, wherein the algorithm is to allow the parameters to adaptively contribute to the determination of flow rate such that one of the parameters applied to a corresponding determination changes with each successive step of receiving a first output thermal signal during the flow rate determining process.

* * * * *